United States Patent [19]
Billings

[11] Patent Number: 6,126,656
[45] Date of Patent: *Oct. 3, 2000

[54] ELECTROSURGICAL CUTTING DEVICE

[75] Inventor: R. Gail Billings, Holladay, Utah

[73] Assignee: Utah Medical Products, Inc., Midvale, Utah

[ * ] Notice: This patent is subject to a terminal disclaimer.

[21] Appl. No.: 08/593,618

[22] Filed: Jan. 30, 1996

[51] Int. Cl.7 .................................................. A61B 17/39
[52] U.S. Cl. ................................................. 606/45; 606/41
[58] Field of Search ........................... 606/39–49, 79–82, 606/113, 167–171

[56] References Cited

U.S. PATENT DOCUMENTS

| | | | |
|---|---|---|---|
| 3,987,795 | 10/1976 | Morrison | 128/303.14 |
| 4,161,950 | 7/1979 | Doss et al. | 128/303.14 |
| 4,196,734 | 4/1980 | Harris | 606/38 |
| 4,198,957 | 4/1980 | Cage | 606/45 |
| 4,485,810 | 12/1984 | Beard | 128/303.1 |
| 4,549,073 | 10/1985 | Tamura et al. | 219/497 |
| 4,589,411 | 5/1986 | Friedman | 606/49 |
| 4,622,966 | 11/1986 | Beard | 128/303.14 |
| 5,013,312 | 5/1991 | Parins et al. | 606/37 |
| 5,171,311 | 12/1992 | Rydell | 606/48 |
| 5,308,311 | 5/1994 | Eggers et al. | 606/28 |
| 5,352,868 | 10/1994 | Denen et al. | 219/501 |
| 5,376,089 | 12/1994 | Smith | 606/42 |
| 5,437,665 | 8/1995 | Munro | 606/47 |
| 5,441,499 | 8/1995 | Fritzsch | 606/45 |
| 5,472,442 | 12/1995 | Klicek | 606/42 |
| 5,702,387 | 12/1997 | Arts et al. | 606/45 |

*Primary Examiner*—Jeffrey R. Jastrzab
*Assistant Examiner*—David Ruddy
*Attorney, Agent, or Firm*—Madson & Metcalf, P.C.

[57] ABSTRACT

An improved electrosurgical cutting device for connection to an electrosurgical generator has a non-conductive support member with a peripheral edge and a conducting member in the form of a wire electrode, distinct from the support member, disposed along at least a portion of the peripheral edge of the support member. The conducting member is electrically connected to an electrosurgical generator suitable for transmitting sufficient high frequency electrical energy to the conducting member, thereby enabling the conducting member to cut body tissue. The support member has a configuration that facilitates the manipulation of body tissue either with or without the presence of electrical energy at the conducting member.

25 Claims, 3 Drawing Sheets

ELECTROSURGICAL CUTTING DEVICE

BACKGROUND OF THE INVENTION

1. Field of the Invention

This invention relates to electrosurgical electrode instruments for surgical cutting of body tissue.

2. Technical Background

Electrosurgical instruments are used extensively in surgical practice and the advantages to their use over conventional non-electrical surgical instruments are well recognized in the practice. A common approach taken in the art of electrosurgery that is effective for both cauterizing and cutting tissue entails the use of a monopolar circuit. A monopolar circuit is composed of an electrosurgical generator with two outlet connections: an active and a dispersive. The dispersive outlet connects to a dispersive pad which is attached to a patient's body. The electrosurgical generator sends high frequency electrical energy through the patient's body by means of the dispersive connection. The active connection is connected to an electrode which is then placed in proximity to or in contact with the body. Thus, the electrical energy present in the body is concentrated to those specific areas in proximity to the electrode. Those cells of the body thus exposed to the concentrated electrical energy are heated and then exploded by sparks arcing from the electrode to the cells. In this manner, the circuit is completed and, depending on further techniques, cauterization or cutting is achieved.

The shape and size of the electrode may vary depending on the purpose of the surgery. Commonly found in the surgical practice are electrosurgical instruments that utilize thin, wire electrodes. Typically, the wire electrodes are configured into needle or loop shapes. Both the needle and the loop electrodes are efficient cutters because their thinness allows the surgeon to concentrate the electrical energy to a very limited region of body tissue, thus fully utilizing the energy in the cutting process and preventing any unnecessary exposure to the electrical energy where cutting or burning of tissue is not desired. The principles that govern the electrosurgical cutting process are well known and the observation that thin wire electrodes are the best cutters is not a surprising conclusion to any knowledgeable practitioner.

However, the wire electrodes are limited in their cutting performance due to their lack of mechanical rigidity and their general fragile nature. This is especially true when the electrodes become hot during the surgical cutting process. Furthermore, it is often desirable for the surgeon to use the cutting electrode, without current applied, as a mechanical tool to separate tissues (i.e., cold or mechanical dissection) that are adjacent to each other but which should not be exposed to the electrical energy of electrosurgical cutting. Naturally, the thin electrodes function poorly in mechanically separating body tissue because they lack sufficient mechanical reinforcement to effect proper dissection.

An electrosurgical instrument that is conveniently used both for electrosurgical cutting and mechanical dissection is the paddle electrode. This elongated, flat electrode has the mechanical strength to allow mechanical dissection and is able to create sufficient current concentration on its edges to accomplish good electrosurgical cutting. However, compared to a needle or wire loop electrode, the paddle electrode is a less efficient cutter because much of the high frequency electrical energy supplied by the electrosurgical generator flows to the body tissue through the sides of the paddle electrode where no exposure or cutting activity is desired. In some circumstances, the current flowing through the sides of the paddle electrode may have a beneficial effect in cauterizing the wound created in cutting through the tissue. However, in most cases, it is a wasteful use of current resulting in an extra burden for the electrosurgical generator and requires a larger power setting of the generator to accomplish the cut. Using a paddle electrode also frequently results in thermal damage to the tissue along the cut and in troublesome sticking of tissue to the sides of the paddle. Nevertheless, the paddle electrode has the advantages of superior mechanical strength and a flat shape that acts as a rudder giving the surgeon a better ability to guide the electrode along a straight or smooth curved line.

One attempt to solve the side conduction problem of the paddle electrode has been to coat the sides of the paddle with plastic, typically Teflon, which diminishes the current conducted out the side and prevents sticking of the tissue to the paddle electrode. This solution is only partially successful because at the high frequencies used for electrosurgery, there is substantial current that is capacitively coupled from the metal of the paddle, through the plastic coating, and to the body tissue. Thus, a more successful and permanent solution has yet to be realized.

From the foregoing, it will be appreciated that it would be an advancement in the art to provide an improved electrosurgical cutting device which realizes the advantages of the wire electrode and paddle electrode and at the same time eliminating their disadvantages. Specifically, it would be an advancement in the art to provide an electrosurgical cutting device which concentrates the electrical energy to a limited area of body tissue, yet has sufficient mechanical rigidity to allow improved cutting performance and to permit mechanical dissection. Yet another advancement in the art is to provide a device with the above features which is simple and economical to manufacture.

Such an electrosurgical cutting device is disclosed and claimed herein.

BRIEF SUMMARY OF THE INVENTION

The present invention provides an electrosurgical cutting device to be used generally in all areas of surgical cutting. The present invention particularly contemplates the use of the electrosurgical cutting device as the active outlet in a monopolar circuit. The present invention is designed to efficiently cut body tissue through the process of cell lysis using heat produced by electrical current concentrated at the site where cutting is desired. In the absence of electrical energy, the device is capable of manipulating or mechanically dissecting body tissue. Compared to conventional paddle electrodes, cutting efficiency is improved by greater concentration of current in the tissues. Tissue thermal damage is reduced by elimination of current dispersed away from the cutting edge. This is accomplished by disposing a conducting member along the outer perimeter of a non-conductive support member. In the preferred embodiment the conducting member comprises a thin, wire electrode. The support member gives the wire electrode additional support, strength, and rigidity which will allow for better cutting. The rigidity provided by the non-conducting support member allows the surgeon better handling in positioning the device and guiding the device to cut along a precise path. Furthermore, with the electrical energy to the conducting member on or off, the support member allows sufficient mechanical strength to manipulate or mechanically dissect body tissue.

The support member is generally of a shape and length suitable to cutting body tissue and may be embodied as a paddle shape with two major surface areas and a width dimension. The support member has a peripheral edge that is sufficiently thin to allow efficient cutting, but thick enough to ensure sufficient strength in the support member. The support member is preferably composed of a rigid, thermally stable, non-conductive material. Thus, the support member retains its strength and utility when exposed to the heat produced by electrical energy passing through the supported conducting member and the adjacent tissue. Furthermore, the support member does not conduct electrical energy, hence electrical energy is not conducted through the major surface areas of the support member, only along the peripheral edge where the conducting member is disposed. Consequently, electrical energy is only applied where the conducting member comes into contact with the body tissue. In a preferred embodiment, the support member is composed of any of a variety of ceramic substrates or plastics commonly known in the art but can be made of any other suitable rigid, non-conductive material.

The electrode embodied in the present invention may include a handle for its manipulation by a surgeon or it may include an adaptable connector on its proximal end which inserts into any of the common surgical electrode handles known in the industry to achieve an electrical connection to the generator through the handle. The support member extends from the distal end of the handle or the adaptable connector. The conducting member may be disposed along a portion of or to the entire exposed peripheral edge of the support member. Those skilled in the art will recognize that many design configurations are possible by altering the shape of the support member and the placement of the conducting member along at least a portion of the peripheral edge of the support member. Although such configurations may result in different methods of handling the device due to different shapes and different points of contact of electrical energy, such variations do not depart from the spirit and scope of the claimed invention.

Connection between the conducting member and an electrosurgical generator is effectuated through the use of a conventional connecting wire or any other suitable means. The connecting wire is of a type suitable for the conduction of high frequency electrical current, and is preferably insulated. The electrosurgical generator is of a type commonly used in the industry for transmitting high frequency electrical energy during electrosurgical operations. In the course of operation, the electrosurgical generator produces a high frequency energy which is transmitted through the connecting wire to the conducting member. The surgeon then guides the conducting member to the specified area of body tissue where the incision is to occur.

BRIEF DESCRIPTION OF THE DRAWINGS

To better understand the invention, a more particular description of the invention will be rendered by reference to the appended drawings. These drawings only provide information concerning typical embodiments of the invention and are not to be considered limiting of its scope. The invention will be described and explained with additional specificity and detail through the use of the accompanying drawings, in which.

DESCRIPTION OF THE PREFERRED EMBODIMENT

Figure 1:
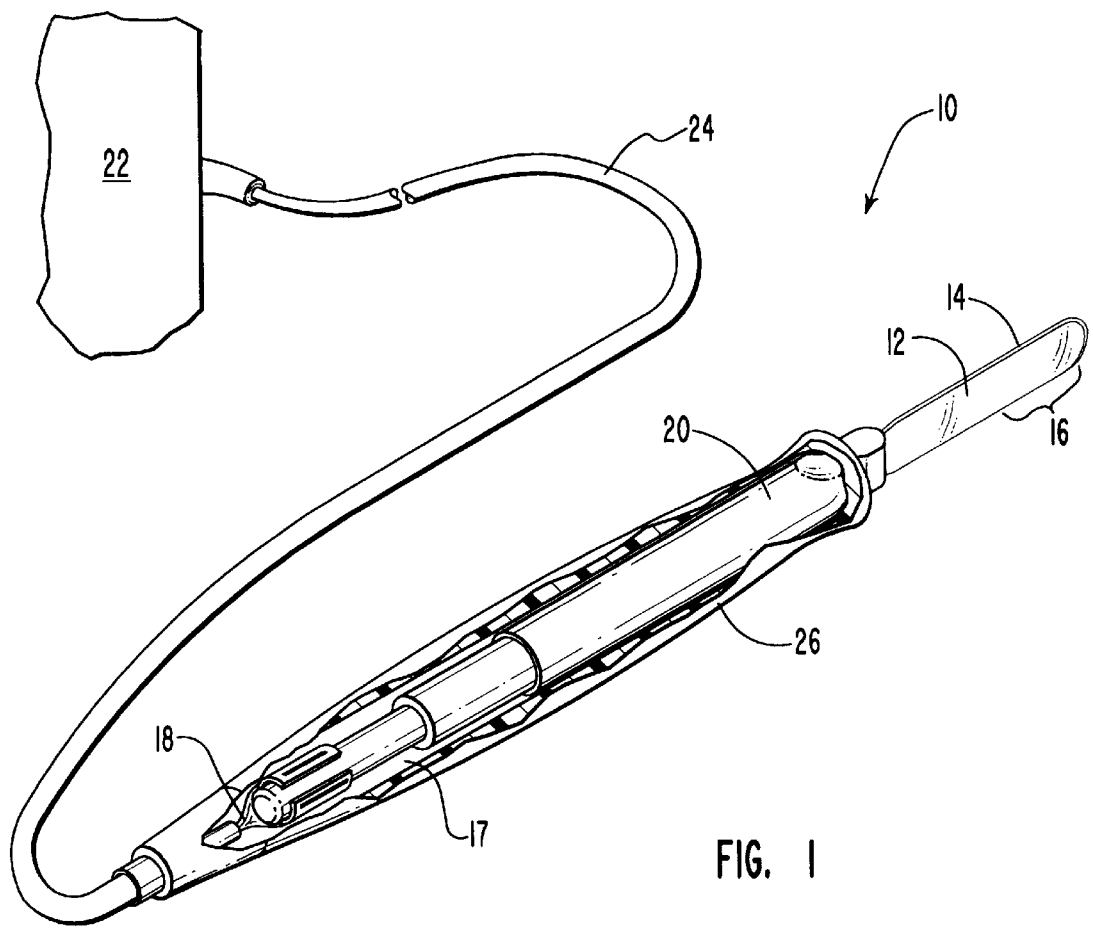
FIG. 1 is a perspective view of one embodiment of the electrosurgical cutting device of the present invention.
Figure 2:
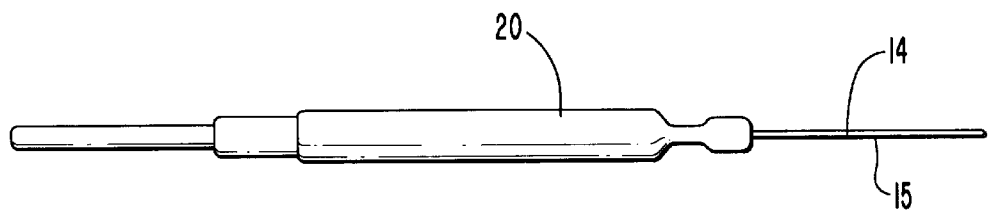
FIG. 2 is a side view illustrating one embodiment of the electrosurgical cutting device of the present invention showing the thickness of the support member and the placement of the conducting member along its peripheral edge.
Figure 3:
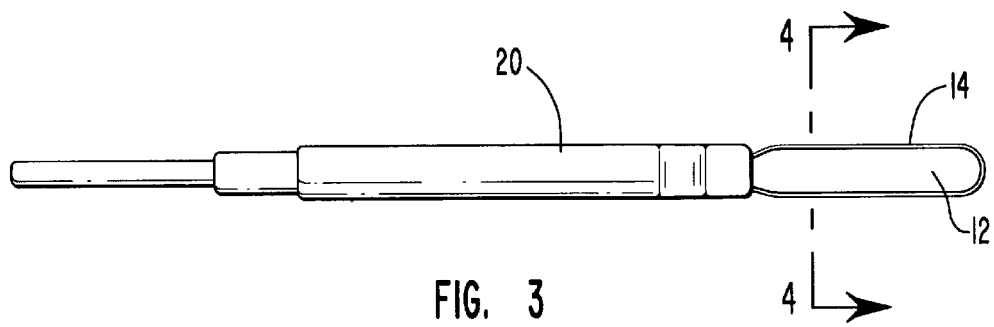
FIG. 3 is a side view of one embodiment of the electrosurgical cutting device of the present invention showing the obverse, or reverse surface area of the support member.
Figure 4:
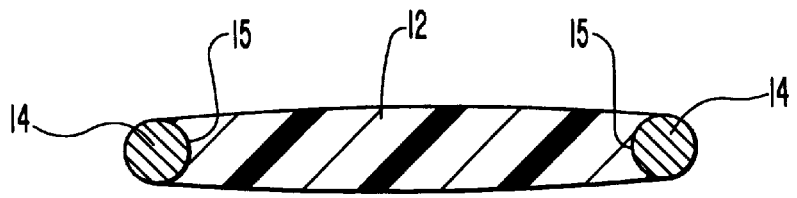
FIG. 4 is an enlarged sectional view of the support member along line 4—4 of FIG. 3.
Figure 7:
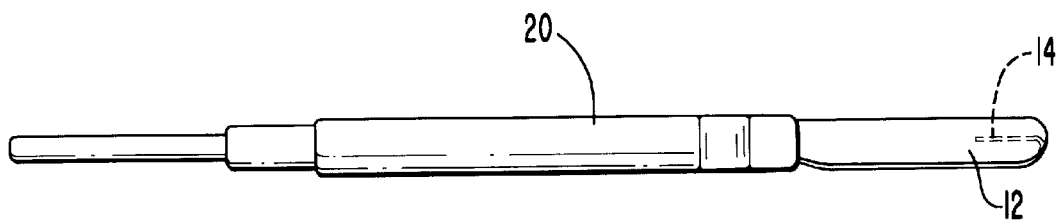
FIG. 7 is a side view of an embodiment of the electrosurgical cutting device with a portion of the conducting member (shown in phantom lines) passing internally through the support member.
Figure 8:
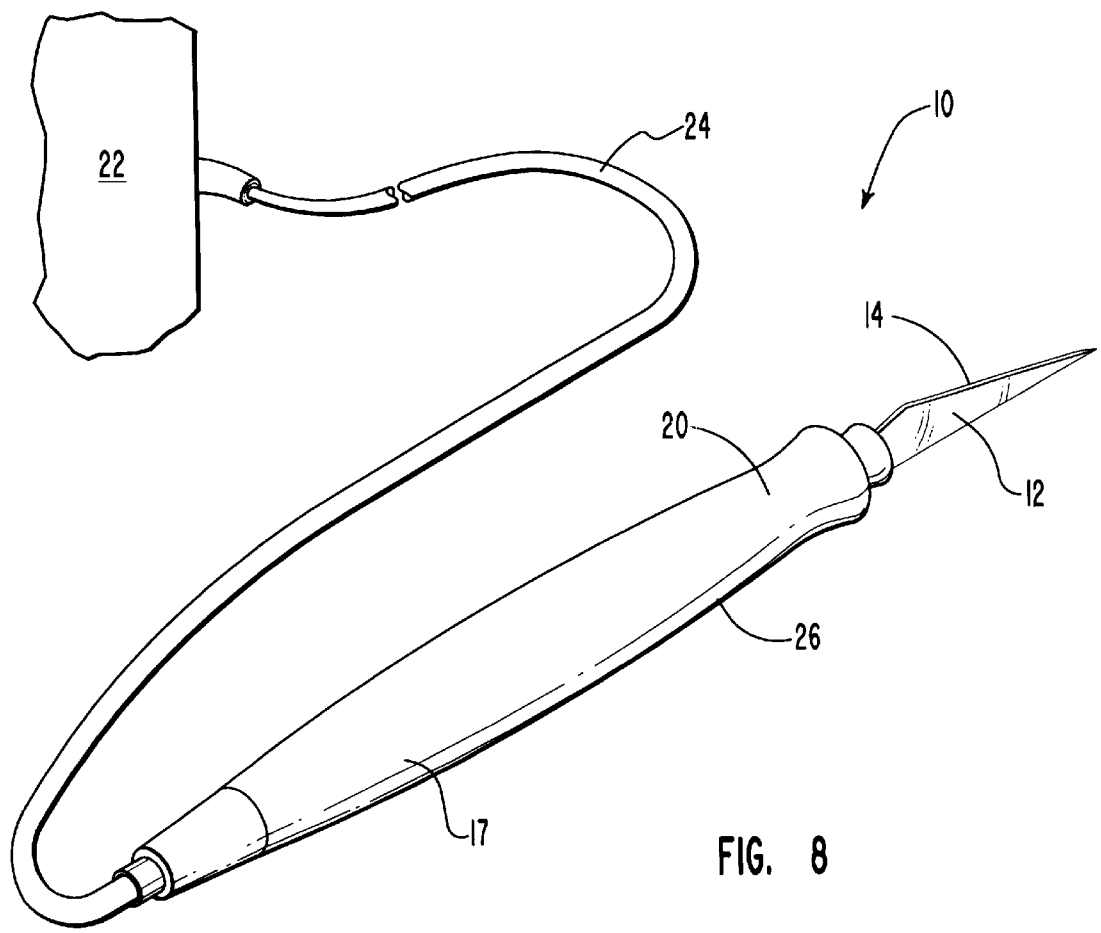
FIG. 8 is a perspective view of an embodiment of the electrosurgical cutting device with the support member extending from the handle.

Reference is now made to the figures wherein like parts are referred to by like numerals throughout. With reference to FIGS. 1, 2, and 3, there is illustrated an electrosurgical cutting device 10 of the present invention. The cutting device 10 may be used as the active outlet of a monopolar circuit. The cutting device 10 comprises a support member 12 composed of a strong, non-conductive material and a conducting member 14. The conducting member 14 is preferably embodied as a wire electrode and primary consideration is given to this embodiment in the specification. However, it is understood, and those skilled in the art will recognize, that other embodiments of the conducting member 14 such as conductive materials in the form of deposits, etchings, or sprays would be included within the scope of the is present invention. Preferably the material for the support member 12 is thermally stable so that the support member 12 will be unaffected by the heat produced by electrical energy passing through the conducting member 14. The material is preferably from any one of a variety of ceramic substrates commonly known and used in the art but can be made of any other suitable material such as plastic. The support member 12 may be configured in various shapes suitable for cutting body tissue, including paddle shapes similar to conventional paddle electrodes with an obverse side, reverse side, width dimension, and a peripheral edge 16. Optionally, the support member 12 may also be configured in a variety of knife blade or scalpel shapes such as shown in FIGS. 7 and 8. The support member 12 is configured with a thin peripheral edge 16 with the conducting member 14 disposed thereon, yet has sufficient mechanical strength to permit cold or mechanical dissection, separating and manipulating the body tissue without conduction of electrical energy. There is sufficient space on the peripheral edge 16 to receive the conducting member 14. Optionally, the support member 12 may be formed with a groove 15 along the peripheral edge 16 in which the conducting member 14 is securely seated as shown in FIG. 4.

The conducting member 14 is separate and distinct from the support member 12 and is composed of a material which is suitable to conduct high frequency electrical energy for cutting body tissue. In a preferred embodiment, the conducting member 14 is composed of tungsten or stainless steel. The conducting member 14 is secured to the peripheral edge 16 of the support member 12, such that the surgeon can easily guide the conducting member 14 to the position of desired contact with the body tissue.

Figure 5:
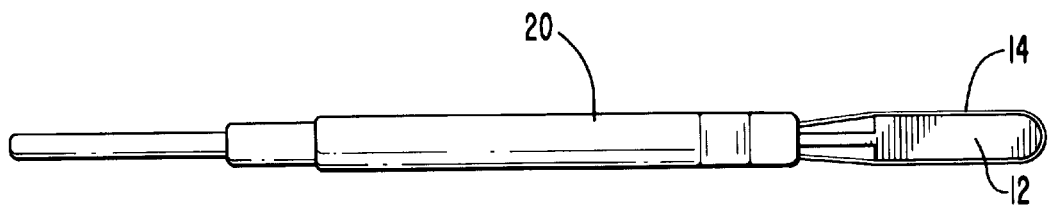
FIGS. 5 and 6 are side views of alternative embodiments of the electrosurgical cutting device with the conducting member encompassing additional fill material other than the support member.
Figure 6:
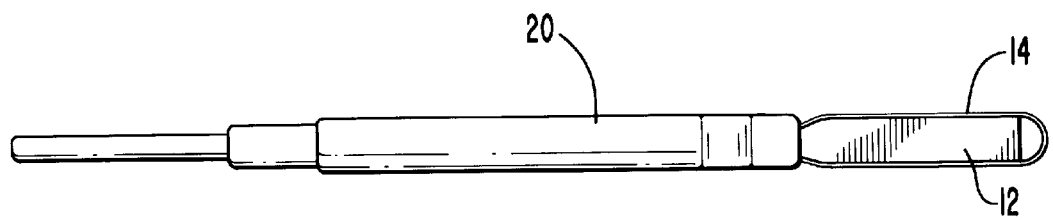

In the preferred embodiment depicted in FIGS. 1–3, the conducting member 14 is embodied as a wire loop electrode with a wire forming a loop around the support member 12. In the preferred embodiment, the conducting member 14 is disposed along the entire exposed peripheral edge 16. However, those skilled in the art will recognize that a variety of configurations and embodiments are possible. For example, as shown in FIGS. 5 and 6, the loop formed by the conducting member 14 may encompass the support member 12 as well as some other fill material, such as air. The conducting member 14 may only be partially disposed along the peripheral edge 16, see FIGS. 7 and 8. In FIG. 7 the conducting member 14 is partially disposed along the peripheral edge 16 and a portion of the conducting member 14 is internal to the support member 12. In FIG. 8, the conducting member 14 the support member 12 is embodied in a scalpel shape and the conducting member 14 is disposed only along the leading edge of the support member 12. These configurations are illustrative of a variety of embodiments which are possible without departing from the scope of the invention.

A typical practice in the art is to have the conducting member 14 attached to one end of a conducting adaptable connector 20. The adaptable connector 20 is engageable with a handle 26, and electrical energy is transmitted from the electrosurgical generator 22 through the handle 26 and adaptable connector 20 to the conducting member 14. FIG. 1 illustrates disposition of the handle 26 and adaptable connector 20 when disposed in electrical communication.

As illustrated in FIG. 1, support member 12 and conducting member 14 extend from the distal end of a conducting adaptable connector 20. The adaptable connector 20 serves two purposes. It engages a source for electrical energy from some conductive carrier such as the electrosurgical generator 22 and transmits the electrical energy to the conducting member 14. It also permits attachment of the support member 12 and conducting member 14 to a handle 26 to facilitate hand-held manipulation of the cutting device 10. The adaptable connector 20 is of a configuration commonly known in the industry and its proximal end is insertable into a receiving handle 26 which is also commonly known in the industry.

The handle 26 receives in mechanical engagement the adaptable connector 20 and accommodates the communication of electrical energy through a connecting wire 18 which exits out the proximal end of the handle 26 and connects to an electrosurgical generator 22. FIG. 1 shows the preferred embodiment of the invention in which the handle 26 is shown with an interior cavity 17 for receiving the connecting wire 18.

The connecting wire 18 connects to the electrosurgical generator 22 and preferably enters in the proximal end or midsection of the handle 26 and passes into the interior cavity 17 of the handle 26, along a longitudinal axis of the handle 26. The connecting wire 18 electrically engages the adaptable connector 20. The connecting wire 18 is insulated and capable of carrying high frequency electrical energy to the conducting member 14 through the adaptable connector 20. In a preferred embodiment, the connecting wire 18 exiting from the electrosurgical generator 22 is shielded within a cable 24 suitable for protecting the connecting wire 18.

The electrosurgical generator 22 is of a type commonly known and used in the industry, and has an adjustable output of high frequency electrical energy. By controlling the output of the electrosurgical generator 22, the operator or surgeon is able to transmit sufficient high frequency electrical energy through the connecting wire 18 to the adaptable connector 20 and to the conducting member 14 to enable the conducting member 14 to cut body tissue.

Those skilled in the art will recognize that many other embodiments are possible without departing from the scope of the invention. For instance, rather than using an adaptable connector 20, the connecting wire 18 may connect directly to the conducting member 14. An embodiment may also forgo the use of an adaptable connector 20 and have the support member 12 and conducting member 14 extend from the distal end of a handle 26 as seen in FIG. 8. In such an embodiment the handle 26 would have means for conducting electrical energy from an electrosurgical generator 22 to the conducting member 14.

It should be appreciated that the apparatus of the present invention is capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States letters patent is:

1. An electrosurgical cutting device for communicating electrically with an electrosurgical generator for use in a monopolar circuit comprising:
   a non-conductive support member having a peripheral edge; and
   a conducting member, distinct from said support member, configured to function as an active outlet in a monopolar circuit for electrosurgical cutting and disposed along at least a portion of the peripheral edge of said support member, said conducting member configured to communicate electrically with only one pole of the electrosurgical generator to receive high frequency electrical energy from the electrosurgical generator, wherein said conducting member forms a wire loop electrode with said support member filling the center of the loop.

2. The electrosurgical cutting device of claim 1 wherein said wire loop electrode comprises a tungsten wire.

3. The electrosurgical cutting device of claim 1 wherein said wire loop electrode comprises a stainless steel wire.

4. The electrosurgical cutting device of claim 1 wherein said support member is composed of thermally stable material.

5. The electrosurgical cutting device as in claim 1 wherein said support member is shaped in the form of a paddle with an obverse side, a reverse side, and peripheral edge.

6. The electrosurgical cutting device of claim 1 wherein said support member is composed of ceramic material.

7. The electrosurgical cutting device as in claim 1 wherein said support member is configured to allow the manipulation of body tissue in the absence of electrical energy to said conducting member.

8. The electrosurgical cutting device of claim 1 wherein said support member is configured with a groove along at least a portion of the peripheral edge of said support member and said conducting member is seated in the groove.

9. The electrosurgical cutting device of claim 1 further comprising an adaptable connector, said adaptable connector having a proximal and distal end, said support member extending from the distal end of said adaptable connector.

10. The electrosurgical cutting device of claim 9 wherein said adaptable connector is configured to engage a handle in electrical and mechanical engagement to facilitate manual manipulation.

11. An electrosurgical cutting device for communicating electrically with an electrosurgical generator for use in a monopolar circuit comprising:

a non-conductive support member having a peripheral edge wherein said support member is configured with a groove along at least a portion of the peripheral edge of said support member;

a conducting member, distinct from said support member, configured to function as an active outlet in a monopolar circuit for electrosurgical cutting and disposed along at least a portion of the peripheral edge of said support member, wherein said conducting member is seated in the groove; and an adaptable connector in electrical communication with said conducting member, said adaptable connector having a proximal and distal end, said support member extending from the distal end of said adaptable connector, wherein said adaptable connector is configured to be in electrical communication with only one pole of the electrosurgical generator to receive high frequency electrical energy from the electrosurgical generator.

12. The electrosurgical device of claim 11 further comprising a handle configured to receive in electrical and mechanical engagement the proximal end of said adaptable connector.

13. The electrosurgical device of claim 12 further comprising a connecting wire which passes through the interior of said handle and allows said adaptable connector to electronically communicate with the electrosurgical generator, thereby allowing the electrosurgical generator to transmit high frequency electrical energy through said adaptable connector to said conducting member to enable said conducting member to cut body tissue.

14. The electrosurgical device of claim 11 wherein said support member is composed of thermally stable material.

15. The electrosurgical device of claim 11 wherein said support member is configured to allow the manipulation of body tissue in the absence of electrical energy to said conducting member.

16. The electrosurgical cutting device of claim 11 wherein a portion of said conducting member is internal to said support member.

17. The electrosurgical cutting device of claim 11 wherein said conducting member comprises a wire electrode.

18. An electrosurgical cutting device for communicating electrically with an electrosurgical generator for use in a monopolar circuit comprising:

a handle having a proximal end and a distal end;

a non-conductive, thermally stable support member extending from the distal end of said handle, said support member having a peripheral edge, said support member being configured to allow the manipulation of body tissue; and a conducting member, distinct from said support member, extending from said handle and configured to function as an active outlet in a monopolar circuit for electrosurgical cutting and, said conducting member disposed along at least a portion of the peripheral edge of said support member, said conducting member configured to communicate electrically with only one pole of the electrosurgical generator to receive high frequency electrical energy from the electrosurgical generator, wherein said conducting member forms a wire loop electrode with said support member filling the center of the loop.

19. The electrosurgical device of claim 18 further comprising a connecting wire for contecting said electrosurgical generator electrically with said conducting member.

20. The electrosurgical device of claim 18 wherein said support member is configured with a groove along at least a portion of the peripheral edge of said support member and said conducting member is seated in the groove.

21. An electrosurgical cutting device for communicating electrically with an electrosurgical generator for use in a monopolar circuit comprising:

a non-conductive support member having a peripheral edge; and a conducting member, distinct from said support member, configured to function as an active outlet in a monopolar circuit for electrosurgical cutting and disposed along at least a portion of the peripheral edge of said support member, said conducting member configured to communicate electrically with only one pole of the electrosurgical generator to receive high frequency electrical energy from the electrosurgical generator, wherein a portion of said conducting member is completely enclosed within said support member.

22. The electrosurgical cutting device of claim 21 wherein said conducting member comprises a wire electrode.

23. The electrosurgical cutting device of claim 21 wherein said support member is composed of thermally stable material.

24. The electrosurgical cutting device of claim 21 wherein said support member is composed of ceramic material.

25. The electrosurgical cutting device of claim 21 wherein said support member is configured with a groove along at least a portion of the peripheral edge of said support member and said conducting member is seated in the groove.

* * * * *